US007231730B1

(12) United States Patent
Ryan et al.

(10) Patent No.: US 7,231,730 B1
(45) Date of Patent: Jun. 19, 2007

(54) INNER WAVE SHOE AND BOOT

(76) Inventors: Sarah Ryan, 314 Gloucester Dr., Glenburnie, MD (US) 21061; Philip Smith, 314 Gloucester Dr., Glenburnie, MD (US) 21061

( * ) Notice: Subject to any disclaimer, the term of this patent is extended or adjusted under 35 U.S.C. 154(b) by 236 days.

(21) Appl. No.: 11/104,867

(22) Filed: Apr. 12, 2005

(51) Int. Cl.
*A61F 5/14* (2006.01)

(52) U.S. Cl. .......... 36/141

(58) Field of Classification Search .......... 36/141; 601/46
See application file for complete search history.

(56) References Cited

U.S. PATENT DOCUMENTS 3,731,674 A 5/1973 Parvin
4,802,463 A 2/1989 Rojas
5,113,850 A * 5/1992 Larremore et al. .......... 601/46
5,592,759 A * 1/1997 Cox .......... 36/141
5,682,690 A * 11/1997 Chang .......... 36/141
5,836,899 A 11/1998 Reilly
5,913,838 A * 6/1999 Reilly .......... 601/58
6,237,256 B1 * 5/2001 Maki et al. .......... 36/140
6,464,654 B1 * 10/2002 Montgomery et al. .......... 601/46
2004/0255490 A1 * 12/2004 Wan et al. .......... 36/137

* cited by examiner

*Primary Examiner*—Ted Kavanaugh

(57) ABSTRACT

A modified athletic shoe that has a motorized massaging apparatus that moves back and forth within the base of the shoe. The massaging apparatus can be turned on and off as desired, and furthermore, is powered by rechargeable batteries that are located within the shoe.

5 Claims, 2 Drawing Sheets

INNER WAVE SHOE AND BOOT

I. BACKGROUND OF THE INVENTION

The present invention concerns that of a new and improved type of athletic shoe.

II. DESCRIPTION OF THE PRIOR ART

U.S. Pat. No. 5,836,899, issued to Reilly, discloses a vibrating massage system for footwear, comprised of vibrators that are mounted in circular beds in the sole.

U.S. Pat. No. 4,802,463, issued to Rojas, discloses an article of footwear comprised of a battery-powered vibrating motor incorporated in a pocket above the sole for massaging the feet of a user.

U.S. Pat. No. 3,731,674, issued to Parvin, discloses a shoe having a battery powered motor for producing vibrations through the feet to promote relation of the nerves and muscles.

III. SUMMARY OF THE INVENTION

The present invention would be a modified athletic foot covering that has a motorized massaging apparatus that moves back and forth within the base of the foot covering. The massaging apparatus can be turned on and off as desired, and furthermore, is powered by rechargeable batteries that are located within the foot covering.

There has thus been outlined, rather broadly, the more important features of a foot covering that the detailed description thereof that follows may be better understood and in order that the present contribution to the art may be better appreciated. There are, of course, additional features of the foot covering that will be described hereinafter and which will form the subject matter of the claims appended hereto.

In this respect, before explaining at least one embodiment of the foot covering in detail, it is to be understood that the foot covering is not limited in its application to the details of construction and to the arrangements of the components set forth in the following description or illustrated in the drawings. The foot covering is capable of other embodiments and being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present foot covering. It is important, therefore, that the claims be regarded as including such equivalent constructions insofar as they do not depart from the spirit and scope of the present invention.

It is therefore an object of the present invention to provide a foot covering which has all of the advantages of the prior art and none of the disadvantages.

It is another object of the present invention to provide a foot covering which may be easily and efficiently manufactured and marketed.

It is another object of the present invention to provide a foot covering which is of durable and reliable construction.

It is yet another object of the present invention to provide a foot covering which is economically affordable and available for relevant market segment of the purchasing public.

Other objects, features and advantages of the present invention will become more readily apparent from the following detailed description of the preferred embodiment when considered with the attached drawings and appended claims.

IV. BRIEF DESCRIPTION OF THE DRAWINGS

V. DESCRIPTION OF THE PREFERRED EMBODIMENT

The present invention would be a modified athletic shoe that has a motorized massaging apparatus that moves back and forth within the base of the shoe. The massaging apparatus can be turned on and off as desired, and furthermore, is powered by rechargeable batteries that are located within the shoe. The shoes are designed to be waterproof.

Figure 1:
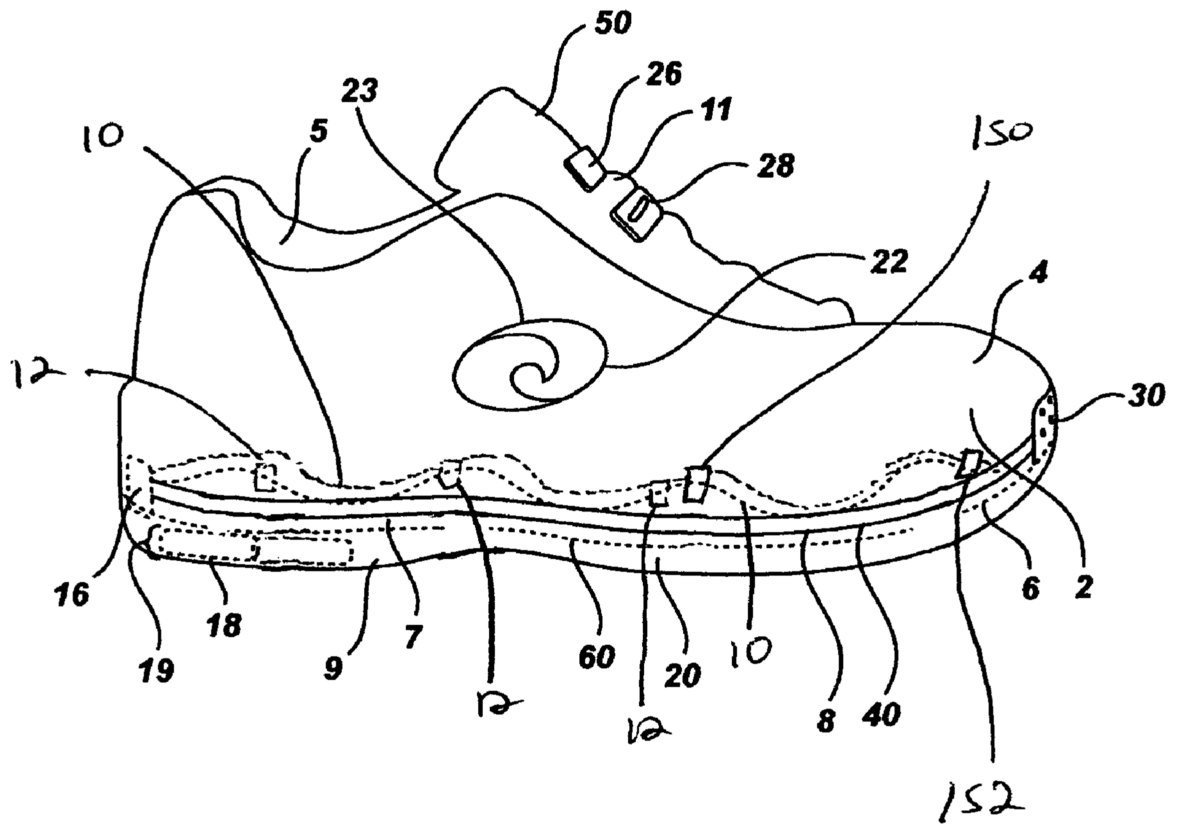
FIG. 1 shows a side view of the athletic shoe.

FIG. 1 shows a side view of the athletic shoe 2. Shoe 2 comprises an outer covering 4 that is attached to a base 6, with the outer covering having a top-mounted hole 5 for insertion of an individual's foot and a plurality of laces 11 for securing the outer covering 4 to an individual's foot. The base 6 comprises an attached sole 7 that is fixedly attached to the outer covering 4 and also comprises a removable base 9 that is removably attached to the attached sole 7. The removable base 9 can be attached or detached as desired. The base 6 has two ends, a front end and a rear end.

A cushion layer 8 is located on the top surface of the base 6, with the cushion layer 8 having two ends, a front end and a rear end. The cushion layer 8 incorporates a volume of gel material 40. Under the cushion layer 8 is a pair of spinning bars 10 with a plurality of bearings 12, which will give an even massage for the whole foot. The spinning bar 10 is driven by a motor 16.

Each of the spinning bars 10 runs lengthwise through the shoe just underneath the cushion layer 8 and has a slight corkscrew shape. In FIG. 1, the spinning bars 10 appear above the cushion layer 8, but this is due to top perspective view. The spinning bars 10 are held in place by a center support 150 and a front support 152.

A motor 16 is incorporated into the rear of the shoe 2, with the motor 16 being powered by at least one battery 18. The battery 18 is preferably a rechargeable battery and are located within a compartment 19 located within the attached sole 7.

Shoe 2 has a reflective material 20 attached to the side of the removable base 9, which is viewable after the removable base 9 is attached to the attached sole 7. Shoe also has a side-mounted pocket 22 attached to the outer covering 4. The outer covering 4 is normally empty, but can retain a color chip 23 that is placed within the pocket 22. The color chip 23 is designed to either hold a clear color or a specific logo that is desired by an individual to effectively "brand" their shoe.

The tongue 50 of the shoe 2 is attached to the outer covering 4 and has a plug-in socket 26 for recharging the batteries 18 located within the compartment 19. The tongue 50 also has a on/off switch 28 that acts as a circuit in between the battery 18 and the motor 16. When the on/off switch 28 is in an "on" mode, the connection between the motor 16 and the battery 18 is closed, thereby allowing the spinning bar 10 to go back and forth from the front end to the rear end of the cushion layer 8. When the on/off switch 28 is in an "off" mode, the connection between the motor 16 and the battery 18 is open, thereby not allowing the spinning bar 10 to rotate and give a massage.

The front end of the outer covering 4 has a plurality of vents 30. These vents 30 allow an individual to wear the shoes and allow the inside of a shoe 2 to "breathe" when they are in use by an individual.

Figure 2:
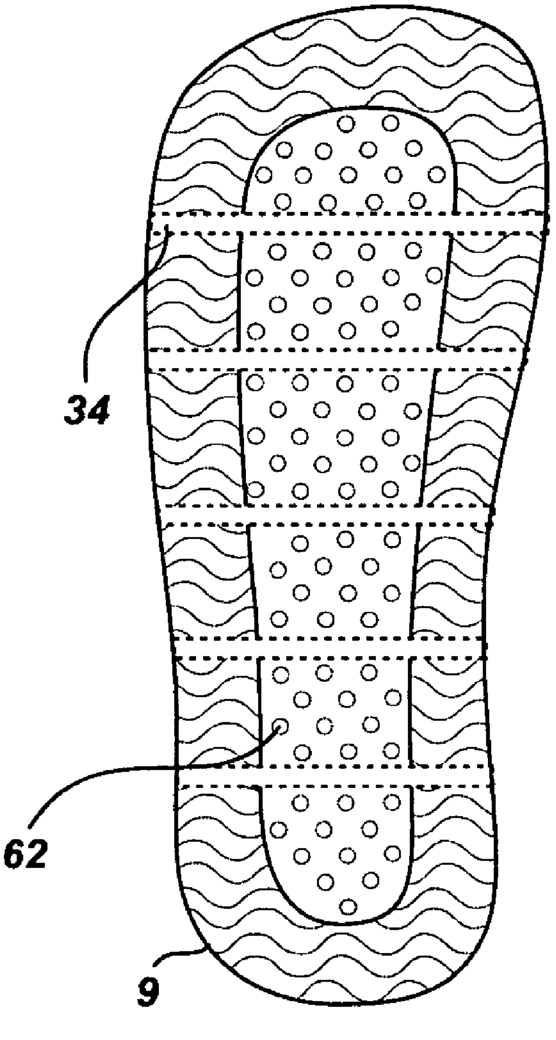
FIG. 2 shows a top view of the removable base used with the athletic shoe.
Figure 3:
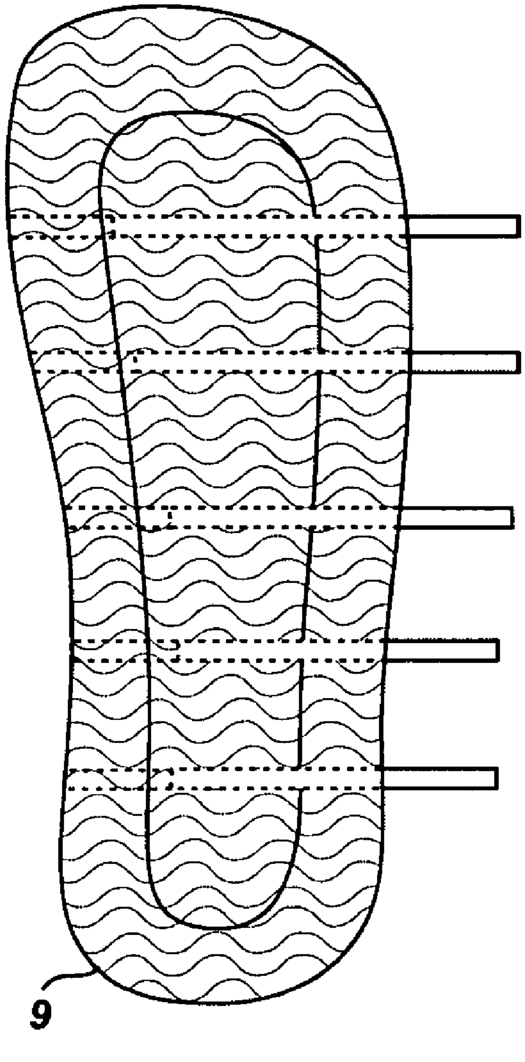
FIG. 3 shows a bottom view of the removable base used with the athletic shoe.

FIG. 2 shows a top view of the removable base 9 used with the athletic shoe 2, while FIG. 3 shows a bottom view of the removable base 9 used with the athletic shoe 2. Removable base 9 is removably attached to the attached sole 7 through a plurality of holding pins 34 that are carefully inserted through the removable base 9. The attached sole 7 has a small extension 60 which fits into the central cup 62 area of the removable base 9, allowing the removable base 9 and the attached sole 7 to be mated to one another.

We claim:

1. An athletic shoe comprising:

(a) a base, the base having two ends, a front end and a rear end, the base further comprising an attached sole, the base further comprising a removable base that is attached to the attached sole, (b) an outer covering attached to the base, the outer covering having a top-mounted hole for insertion of an individual's foot, the outer covering also comprising a plurality of laces for securing the outer covering to an individual's foot, (c) a cushion layer located on the top surface of the base, (d) a volume of gel material located within the cushion layer, (e) a pair of spinning bars located underneath the cushion layer, (f) a plurality of ball bearings mounted on each of the spinning bars, (g) a motor incorporated into the rear end of the athletic shoe, the motor attached to each of the spinning bars, (h) power means for providing power to the motor, (i) a tongue attached to the outer covering, (j) a plug-in socket attached to the tongue, the plug-in socket designed to allow an electrical connection to recharge the batteries, (k) an on/off switch located on the tongue, the on/off switch acting as a circuit in between the battery and the motor, (l) wherein the spinning bar will move back and forth within the cushion layer back and forth between the front end of the cushion layer and the rear end of the cushion layer.

2. An athletic shoe according to claim 1 wherein the athletic shoe further comprises reflective material, the reflective material being attached to the side of the removable base.

3. An athletic shoe according to claim 2 wherein the athletic shoe further comprises at least one side-mounted pocket that is attached to the outer covering.

4. An athletic shoe according to claim 3 wherein the athletic shoe further comprises at least one color chip that is inserted into the side-mounted pocket that is attached to the outer covering.

5. An athletic shoe according to claim 4 wherein the athletic shoe further comprises a plurality of vents located near the front end of the outer covering.

* * * * *